United States Patent [19]
Matsuo et al.

[11] Patent Number: 4,772,753
[45] Date of Patent: Sep. 20, 1988

[54] METHOD FOR PRODUCING CYCLOPROPANECARBOXYLIC ACID DERIVATIVES

[75] Inventors: Noritada Matsuo, Rochester, N.Y.; Kazunori Tsushima, Nishinomiya, Japan

[73] Assignee: Sumitomo Chemical Company, Limited, Osaka, Japan

[21] Appl. No.: 82,942

[22] Filed: Aug. 7, 1987

Related U.S. Application Data

[62] Division of Ser. No. 842,665, Mar. 21, 1986, abandoned.

[30] Foreign Application Priority Data

Apr. 5, 1985 [JP] Japan ................................. 60-73290
Apr. 5, 1985 [JP] Japan ................................. 60-73292
Apr. 8, 1985 [JP] Japan ................................. 60-75034

[51] Int. Cl.$^4$ ............................................. C07C 49/16
[52] U.S. Cl. ................................... 568/419; 562/506
[58] Field of Search ......................................... 568/419

[56] References Cited

U.S. PATENT DOCUMENTS

| 2,865,967 | 12/1958 | Bavley et al. | 568/419 |
| 4,406,909 | 9/1983 | Kramer et al. | 568/419 |
| 4,423,243 | 12/1983 | Jautelat | 560/124 |
| 4,460,793 | 7/1984 | Jautelat et al. | 568/405 |
| 4,487,776 | 12/1984 | Elbe et al. | 568/419 |
| 4,507,496 | 3/1985 | Jautelat | 560/266 |
| 4,582,856 | 4/1986 | Lautzsch | 560/124 |
| 4,619,940 | 10/1986 | Elbe et al. | 568/419 |

FOREIGN PATENT DOCUMENTS 941564 11/1963 United Kingdom.

OTHER PUBLICATIONS

Kramer et al., Chem. Abst., vol. 101, #1109274 (1984).
Schamp et al., Chem. Abst., vol. 83, #177915s (1975).
Khayat et al., Chem. Abst., vol. 70, #11481d (1969).
Olah, "Friedel-Crafts and Related Reactions," vol. III, part 2, pp. 1033–1071, 1107–1131 & 1136–1152 (1964).
March, "Advanced Organic Chemistry; Reactions, Mechanisms, and Structure," pp. 458–459 (1968).
Patent Abstracts of Japan, Unexamined Applications, C section, vol. 2, No. 43, Mar. 23, 1978 (Kokai 62-151 148).

Primary Examiner—James H. Reamer
Attorney, Agent, or Firm—Stevens, Davis, Miller & Mosher

[57] ABSTRACT

A method for producing 2,2,3,3-tetramethylcyclopropane-1-carboxylic acid and intermediate compounds thereof. The 2,2,3,3-tetramethylcyclopropane-1-carboxylic acid is a very useful intermediate for synthesizing insecticidal and acaricidal compounds of pyrethroid type.

1 Claim, No Drawings

METHOD FOR PRODUCING CYCLOPROPANECARBOXYLIC ACID DERIVATIVES

This is a division of application Ser. No. 842,665, filed Mar. 21, 1986, now abandoned.

The present invention relates to a method for producing 2,2,3,3-tetramethylcyclopropane-1-carboxylic acid (hereinafter referred to as tetramethyl acid).

The tetramethyl acid is a compound represented by the formula (I),

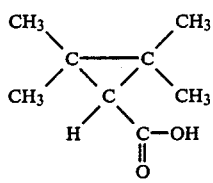   (I)

and it is an acid moiety of pyrethroid type insecticidal and acaricidal compounds, for example, such as fenpropathrin represented by the formula,

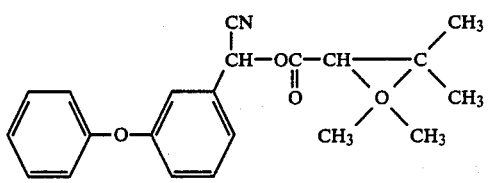

being a very useful intermediate.

The so far well-known representative method for synthesizing tetramethyl acid includes reacting 2,3-dimethyl-2-butene with ethyl diazoacetate and subsequently hydrolyzing the resulting ethyl 2,2,3,3-tetramethylcyclopropane-1-carboxylate, as described below [Matsui, et al., Agr. Biol. Chem., 31, 1143 (1967)]. This method has an advantage that the desired product is obtained by a short process, but it needs to use ethyl diazoacetate having a potential danger of explosion, which is accompanied by a disadvantage that special attention to safety is indispensable for mass production on a commercial scale.

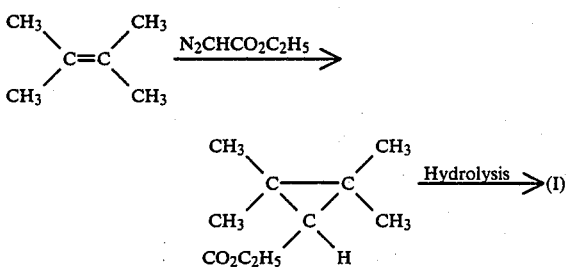

Under the situation like this, the present inventors extensively studied methods for producing tetramethyl acid represented by the foregoing formula (I), and as a result, found that said acid can be produced very advantageously by using a novel halogenoketone compound represented by the general formula (II),

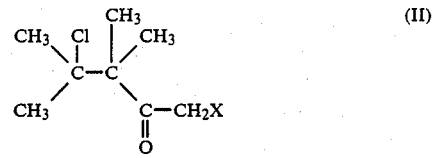   (II)

wherein X represents a chlorine or bromine atom, as an intermediate material and reacting this compound with an alkali hydroxide. The present inventors thus attained to the present invention.

The halogenoketone compound represented by the general formula (II) can be obtained by the halogenation (chlorination or bromination) of a novel ketone compound represented by the formula (III),

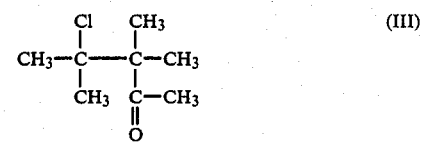   (III)

and said ketone compound can be obtained by reacting 2,3-dimethyl-2-butene with acetyl chloride in the presence of a Lewis acid.

According to the method of the present invention, 2,2,3,3-tetramethylcyclopropane-1-carboxylic acid can be obtained from 2,3-dimethyl-2-butene in good efficiency, as described below:

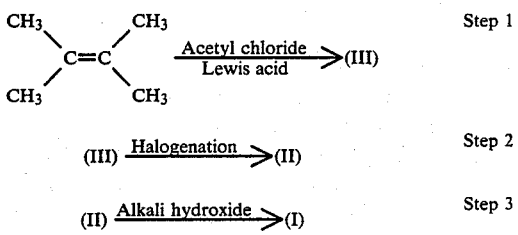

According to the method of the present invention, the new synthetic process can be conducted by using more economical and readily available starting materisls than those of the conventional method and the handling of the dangerous intermediate can be avoided, therefore the method of the present invention is very advantageous as a method used on a commercial scale.

Next, the method of the present invention will be illustrated in detail for each step of the method.

Step 1:

Lewis acid used in this step includes metal chlorides such as ferric chloride, zinc chloride, aluminum chloride, stannic chloride, antimony trichloride, etc. Its amount used is in a range of 0.001 to 1 mole based on 1 mole of 2,3-dimethyl-2-butene. The reaction temperature depends upon the amount of Lewis acid used, being in a range of $-50°$ to $30°$ C, but generally, a range of $-20°$ to $10°$ C is preferred in terms of yield.

The reaction time depends upon the kind and amount of Lewis acid used and the reaction temperature, but this reaction generally proceeds very rapidly, so that the reaction time is not usually more than 10 hours, preferably not more than 2 hours.

Also, the amount of acetyl chloride used is generally in a range of 1.0 to 1.5 moles based on 1 mole of 2,3-dimethyl-2-butene.

For performing this reaction more smoothly, inert solvents such as dichloromethane, dichloroethane, etc. may be used together.

Step 2:

The chlorination or bromination in this step can be performed by various halogenating reagents such as, for example, chlorine, bromine, sulfuryl chloride, phosphorus pentabromide, N-bromosuccinimide, etc. Its amount used is generally 0.7 to 1.5 times by mole based on 1 mole of 3,3,4-trimethyl-4-chloro-2-pentanone.

The solvent usable in this reaction includes water, methanol, acetic acid, dichloromethane, chloroform, etc.

The reaction temperature is generally 0° to 60° C. The reaction time depends upon the kinds of the solvent and chlorinating or brominating agent as well as the reaction temperature, but generally, it is 1 to 24 hours. For performing the reaction more smoothly, a catalytic amount of hydrogen chloride or hydrogen bromide, or a dehydrohalogenating agent such as amines, calcium carbonate, potassium chlorate, etc. may be added to the reaction system.

Step 3:

The most general alkali hydroxide used in this step is sodium hydroxide, potassium hydroxide, etc. Its amount used is in a range of 2 to 15 moles based on 1 mole of the halogenoketone compound represented by the general formula (II).

In the reaction, polar solvents such as water, methanol, ethanol, tetrahydrofuran, dioxane, etc. are generally used alone or in combination as a reaction solvent. It is however possible to carry out this reaction, for example, in a two-phase system such as toluene-water in the presence of a phase transfer catalyst such as quaternary ammonium salt.

The reaction temperature is generally 20° to 100° C.

The present invention will be illustrated in more detail with reference to the following examples.

EXAMPLE 1

After dissolving 20.0 g (0.238 mole) of 2,3-dimethyl-2-butene in 50 ml of 1,2-dichloroethane, 20.5 g (0.261 mole) of acetyl chloride was added, and then 3.2 g (0.0235 mole) of zinc chloride was added portionwise at 0° C with stirring and ice-cooling. At that time, a rise in the inner temperature was observed, but the temperature of the reaction mixture was controlled to 5° C or below. After stirring for further 30 minutes at 0° to 5° C, the reaction mixture was poured into ice water, and separated. The 1,2-dichloroethane layer was washed with water, dried over magnesium sulfate and concentrated (at ca. 80° C/70 mmHg) to obtain 29.0 g of a pale yellow oil as residue (yield, 75%).

This product was identified to be the desired 3,3,4-trimethyl-4-chloro-2-pentanone by NMR spectrum.

This compound has a boiling point of 105°–110° C. 55 mmHg. But, a part of this compound tends to be dehydrochlorinated on distillation to lower the yield, so that it is desirable to stop the distillation at the point when low-boiling fractions have been distilled off.

NMR spectrum (CDCl$_3$):
δ(ppm) 1.30(s, 6H), 1.60(s, 6H), 2.28(s, 3H)

EXAMPLE 2

After dissolving 8.0 g of 3,3,4-trimethyl-4-chloro-2-pentanone in 30 ml of dichloromethane, two drops of dicyclohexylamine were added, and then 10.0 g of sulfuryl chloride was added dropwise at 0° C. After addition, the reaction solution was stirred at 20° C for 24 hours, poured into ice water and extracted with dichloromethane. The dichloromethane layer was washed with water, dried over magnesium sulfate and concentrated. The residue obtained was column-chromatographed on silica gel to obtain 6.1 g of 1,4-dichloro-3,3,4-trimethyl-2-pentanone (a compound of the foregoing formula (II) wherein a substituent X is a chlorine atom) as a pale yellow oil.

$n_D$ 1.4773 (25.5° C)

NMR spectrum (CDCl$_3$)
δ(ppm) 1.37(s, 6H), 1.62(s, 6H), 4.55(s, 2H)

EXAMPLE 3

2.2 Grams of 3,3,4-trimethyl-4-chloro-2-pentanone was dissolved in 15 ml of methanol, and 2.50 g (1.2 times by mole) of bromine was added dropwise at 20° C. After stirring for 1 hour, the reaction solution was poured into ice water and extracted twice with dichloromethane. The dichloromethane layer was dried over anhydrous magnesium sulfate and concentrated to obtain 3.1 g of the desired 1-bromo-4-chloro-3,3,4-trimethyl-2-pentanone (a halogeno-ketone compound of the foregoing formula (II) wherein a substituent X is a bromine atom) (yield, 96%).

$n_D$ 1.5000 (21.5° C)

NMR spectrum (CDCl$_3$)
δ(ppm) 1.37(s, 6H), 1.59(s, 6H), 4.30(s, 2H)

EXAMPLE 4

A solution of 2.7 g of 1,4-dichloro-3,3,4-trimethyl-2-pentanone in 10 ml of tetrahydrofuran was added dropwise at 40° C to a solution comprising 6.0 g of sodium hydroxide, 50 ml of water and 35 ml of tetrahydrofuran. After addition, the reaction mixture was stirred at 25° C for further 12 hours, poured into ice water and extracted with ether to separate the neutral portion. The aqueous solution was acidified with hydrochloric acid and extracted twice with ether. The ether layer was washed with an aqueous sodium chloride solution and dried over magnesium sulfate. The ether was removed by evaporation to obtain 1.60 g of a white crystal (yield, 82.2%).

This product has a melting point of 119.8° C and agrees with 2,2,3,3-tetramethylcyclopropane-1-carboxylic acid synthesized from ethyl diazoacetate and 2,3-dimethyl-2-butene [Matsui, Kitahara, et al., Agr. Biol. Chem., Vol. 31, 1143 (1967)].

EXAMPLE 5

A solution of 4.1 g of 1-bromo-4-chloro-3,3,4-trimethyl-2-pentanone in 10 ml of 1,4-dioxane was added dropwise at 30° C to a solution comprising 3.3 g of potassium hydroxide, 30 ml of water and 20 ml of dioxane, and the resulting solution was stirred at 20° C for 15 hours. Thereafter, the reaction solution was worked up in the same manner as in Example 1 to obtain 1.8 g of the desired 2,2,3,3-tetramethylcyclopropane-1-carboxylic acid as a white crystal (yield, 76%).

What is claimed is:

1. A halogenoketone compound represented by the general formula,

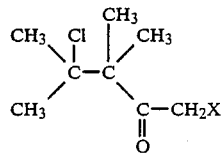

wherein X represents a chlorine or bromine atom.

* * * * *